(12) United States Patent
Pichereau et al.

(10) Patent No.: US 11,860,344 B2
(45) Date of Patent: Jan. 2, 2024

(54) METHOD FOR COMPARING OPTICAL LENSES, ASSOCIATED CONTROL MODULE AND SYSTEM

(71) Applicant: SiVIEW, Marcoussis (FR)

(72) Inventors: Laure Pichereau, Marcoussis (FR); Nathalie Guillemain, Saint Leu la Foret (FR)

(73) Assignee: SIVIEW, Marcoussis (FR)

(*) Notice: Subject to any disclaimer, the term of this patent is extended or adjusted under 35 U.S.C. 154(b) by 664 days.

(21) Appl. No.: 16/971,923

(22) PCT Filed: Feb. 21, 2019

(86) PCT No.: PCT/EP2019/054344
§ 371 (c)(1),
(2) Date: Aug. 21, 2020

(87) PCT Pub. No.: WO2019/162394
PCT Pub. Date: Aug. 29, 2019

(65) Prior Publication Data
US 2021/0088761 A1  Mar. 25, 2021

(30) Foreign Application Priority Data

Feb. 23, 2018 (FR) .................. 1851617

(51) Int. Cl.
*A61B 3/00* (2006.01)
*G02B 13/18* (2006.01)
(Continued)

(52) U.S. Cl.
CPC ............ *G02B 13/18* (2013.01); *A61B 3/0033* (2013.01); *A61B 3/0041* (2013.01); *A61B 3/04* (2013.01);
(Continued)

(58) Field of Classification Search
CPC ......... A61B 3/103; A61B 3/04; A61B 3/0033; A61B 3/0041
See application file for complete search history.

(56) References Cited

U.S. PATENT DOCUMENTS

2006/0050238 A1  3/2006 Nakamura et al.
2020/0069174 A1* 3/2020 Marin ................. A61B 3/0058

FOREIGN PATENT DOCUMENTS

| EP | 1 138 253 A2 | 10/2001 |
|---|---|---|
| WO | WO 2016/142363 A1 | 9/2016 |
| WO | WO 2017/019771 A1 | 2/2017 |

OTHER PUBLICATIONS

Tampoya, Jeremiah. "Topcon Topcon CV-5000 Auto Phoropter Tutorial with RevolutionEHR Integration." YouTube, YouTube, Jan. 26, 2018, https://www.youtube.com/watch?v=jCxnG-Q_eg0 (Year: 2018).*

(Continued)

*Primary Examiner* — Darryl J Collins
*Assistant Examiner* — Matthew Y Lee
(74) *Attorney, Agent, or Firm* — Pillsbury Winthrop Shaw Pittman LLP (57) ABSTRACT

A method for comparing first and second optical lenses such that when a control module receives a selection suggesting the first optical lens for the first time, a suggestion for the second optical lens is selected on a selection screen and no validation symbol is selected on the selection screen; when the control module receives the selection of the suggested second optical lens, the suggested first optical lens is selected on the selection screen and first and second validation symbols is selected on the selection screen, the first symbol indicating that the first and second optical lenses are identical, and the second symbol indicating that the second optical lens is better than the first optical lens; when the control module receives the selection of the suggested first (Continued)

optical lens for the second time or more, the suggested second optical lens is selected on the selection screen.

10 Claims, 3 Drawing Sheets (51) Int. Cl.
*G02B 7/02* (2021.01)
*G02C 7/02* (2006.01)
*A61B 3/04* (2006.01)
*A61B 3/103* (2006.01)

(52) U.S. Cl.
CPC .............. *A61B 3/103* (2013.01); *G02B 7/023* (2013.01); *G02C 7/02* (2013.01)

(56) References Cited

OTHER PUBLICATIONS

Topcon; User Manual Compu-Vision CV-5000; Mar. 1, 2013; 220 pages (Year: 2013).*
Topcon; Instruction Manual CV 1Dial Controller KB-50; Apr. 1, 2008; 90 pages (Year: 2009).*
International Search Report as issued in International Patent Application No. PCT/EP2019/054344, dated May 13, 2019.

* cited by examiner

METHOD FOR COMPARING OPTICAL LENSES, ASSOCIATED CONTROL MODULE AND SYSTEM

CROSS-REFERENCE TO RELATED APPLICATIONS

This application is the U.S. National Stage of PCT/EP2019/054344, filed Feb. 21, 2019, which in turn claims priority to French patent application number 1851617 filed Feb. 23, 2018. The content of these applications are incorporated herein by reference in their entireties.

TECHNICAL FIELD OF THE INVENTION

The field of the invention is that of eyesight examinations which, conducted on a subject, make it possible to determine if said subject needs a correction and which correction.

The invention more specifically pertains to a method for comparing optical lenses by means of an automatic refractor head controlled by a control module, for example during an eyesight examination or during a simple verification of the visual correction worn. The invention also relates to a module for controlling an automatic refractor head for the implementation of the method for comparing optical lenses as well as a system comprising the control module and a selection screen for the implementation of the method for comparing optical lenses.

PRIOR ART

An eyesight examination of a subject starts by an objective refraction measurement and continues by a subjective refraction measurement.

The objective refraction measurement is generally carried out by an operator by means of an autorefractometer. Alternatively to the use of an autorefractometer, a manual skiascopy technique is sometimes used. Failing this, the operator may start from the preceding correction of the examined subject.

During the subjective refraction measurement, the operator has different visual corrections tested by the examined subject by means of suitable equipment which may be:
 a pair of test glasses with test lenses,
 a manual refractor head or
 an automatic refractor head.

In the first case, the operator manually changes the test lenses of the pair of test glasses. With a refractor head, the operator scrolls different optical lenses in front of the eyes of the examined subject, by means of thumbwheels in the case of a manual refractor head or via a control console in the case of an automatic refractor head.

In the course of such a subjective refraction measurement or during a verification of the visual correction worn, when the operator needs to have the examined subject compare two optical lenses, he begins by arranging a first optical lens in front of an eye of the examined subject while said subject observes a reading screen on which one or more test symbols are displayed, then he replaces the first optical lens by a second optical lens while the examined subject still observes the same reading screen, before potentially returning to the first optical lens, etc. After one or more tests on each of the two optical lenses, the examined subject states whether he prefers an optical lens and which as a function of what he has observed on the reading screen with each of the two optical lenses. The operator next continues the subjective refraction measurement or the verification of the correction worn on the basis of the preferred lens indicated by the examined subject or by taking account of the fact that the two lenses are equivalent from the point of view of the examined subject.

There exists however a risk of error by the operator in the selection of the preferred lens of the examined subject, in the event of poor understanding between the examined subject and the operator. For example, a confusion may arise due to switching rapidly from one optical lens to the other or instead if the operator changes optical lens at the precise moment when the examined subject starts to speak. If he has a doubt, the operator can check his understanding with the examined subject. Conversely, the examined subject cannot verify that the selection of the operator is correct. At the same time, such a comparison is generally only one step of an eyesight examination or a verification of visual correction worn and it is desirable to be able to proceed quickly. Furthermore, in the event of error, the eyesight examination or the verification of visual correction worn risks not being completed or taking more time to be completed or being completed with an erroneous result.

A solution is thus sought enabling, notably within the context of an eyesight examination or a verification of a visual correction worn, to compare two optical lenses rapidly and without being mistaken on the optical lens retained.

DESCRIPTION OF THE INVENTION

In this context, the invention aims to overcome all or part of the drawbacks of the prior art identified above.

For this purpose, a first aspect of the invention relates to a method for comparing first and second optical lenses by means of an automatic refractor head controlled by a control module, the method comprising the following steps according to which the control module:
 displays on a selection screen a proposal for a first optical lens and a proposal for a second optical lens;
 receives a selection of the proposal for the first optical lens;
 arranges the first optical lens in a slot of the automatic refractor head on reception of the selection of the proposal for the first optical lens;
 receives a selection of the proposal for the second optical lens;
 arranges the second optical lens in the slot of the automatic refractor head on reception of the selection of the proposal for the second optical lens;
 displays on the selection screen a plurality of validation symbols each indicating a possible result of the comparison;
the method being such that:
 when the control module receives the selection of the proposal for the first optical lens for the first time, the proposal for the second optical lens is selectable on the selection screen and no validation symbol is selectable on the selection screen;
 when the control module receives the selection of the proposal for the second optical lens, the proposal for the first optical lens is selectable on the selection screen and first and second validation symbols are selectable on the selection screen, the first symbol indicating that the first and second optical lenses are the same and the second symbol indicating that the second optical lens is better than the first optical lens;
 when the control module receives the selection of the proposal for the first optical lens for the second time or more, the proposal for the second optical lens is selectable on the selection screen and the first symbol and a third symbol are selectable on the selection screen, the third symbol indicating that the first optical lens is better than the second optical lens.

A second aspect of the invention relates to a module for controlling an automatic refractor head for the implementation of a method for comparing first and second optical lenses according to the first aspect of the invention, the control module having:

means for displaying simultaneously on a selection screen a proposal for a first optical lens, a proposal for a second optical lens and all or part of a plurality of validation symbols each indicating a possible result of a comparison between the first and second optical lenses;

means for receiving a selection of the proposal for the first or the second optical lens or a validation symbol;

means for, on reception of the selection of the proposal for the first or the second optical lens, arranging said first or second optical lens in a slot of the automatic refractor head;

the means for displaying on the selection screen and the means for receiving a selection being such that:

when the control module receives the selection of the proposal for the first optical lens for the first time, the proposal for the second optical lens is selectable on the selection screen and no validation symbol is selectable on the selection screen;

when the control module receives the selection of the proposal for the second optical lens, the proposal for the first optical lens is selectable on the selection screen and first and second validation symbols are selectable on the selection screen, the first symbol indicating that the first and second optical lenses are the same and the second symbol indicating that the second optical lens is better than the first optical lens;

when the control module receives the selection of the proposal for the first optical lens for the second time or more, the proposal for the second lens is selectable on the selection screen and the first symbol and a third symbol are selectable on the selection screen, the third symbol indicating that the first optical lens is better than the second optical lens.

A third aspect of the invention relates to a system for the implementation of a method for comparing first and second optical lenses according to the first aspect of the invention, comprising a module for controlling an automatic refractor head according to the second aspect of the invention as well as a selection screen.

Apart from the characteristics that have been mentioned in the preceding paragraphs, the method for comparing first and second optical lenses according to the first aspect of the invention, the control module according to the second aspect of the invention and the system according to the third aspect of the invention may have one or more complementary characteristics among the following, considered individually or according to all technically possible combinations thereof.

When the second step takes place for the first time, it is carried out automatically by the control module without intervention of an operator.

When the control module receives the selection of the proposal for the first optical lens for the first time, the control module displays no validation symbol on the selection screen.

When the control module receives the selection of the proposal for the second optical lens, the control module displays the first and second validation symbols but not the third validation symbol.

When the control module receives the selection of the proposal for the first optical lens for the second time or more, the control module displays the first and third validation symbols but not the second validation symbol.

The system according to the third aspect of the invention also comprises a reading screen, the selection screen and the reading screen being two distinct screens or a single and same screen.

BRIEF DESCRIPTION OF THE FIGURES

Other characteristics and advantages of the invention will become clear on reading the description that follows, with reference to the appended figures.

For greater clarity, identical or similar elements are marked by identical reference signs in all of the figures.

DETAILED DESCRIPTION OF AT LEAST ONE EMBODIMENT

A first aspect of the invention relates to a method for comparing first and second optical lenses by means of an automatic refractor head controlled by a control module. A second aspect of the invention relates to a module for controlling an automatic refractor head for the implementation of the method for comparing first and second optical lenses according to the first aspect of the invention. A third aspect of the invention relates to a system comprising the control module according to the second aspect of the invention and a selection screen for the implementation of the method according to the first aspect of the invention.

Definitions

Within the scope of the present invention, "optical lens" is taken to mean an optical element of quality suited to the production of prescription glasses, without prejudicing the material of which it is made and which may notably be glass or plastic. The terms "ophthalmic lens" or "corrective lens" may also be employed. The term "optical lens" may also be employed strictly speaking, providing it is indeed interpreted in the sense of an optical element of quality suited to the production of prescription glasses, as opposed to a corneal lens or contact lens.

Within the scope of the present invention, "refractor head" is taken to mean a support comprising first and second slots, one for each eye, each being able to receive an element which is either an opaque mask, or an optical lens. Within the scope of the present invention, "optical lens arranged in a slot of the refractor head" is taken to mean either a single optical lens, or a combination of several optical lenses, enabling a certain optical correction to be made. The refractor head is intended to be placed in front of the examined subject in such a way that the examined subject looks at, through the first and second slots, one or more test symbols displayed on a reading screen in order to read them or to identify them.

"Automatic refractor head" is taken to mean a refractor head for which the successive arrangement of different elements in the first and second slots is done by an operator via the control module. A step of arranging an element in a slot may begin if appropriate by a step of removing a preceding element from said slot.

Within the scope of the method for comparing optical lenses according to the first aspect of the invention, the automatic refractor head may be used in a right eye monocular test, in a left eye monocular test or in a binocular test. In a right eye monocular test, an optical lens is arranged in the slot corresponding to the right eye whereas a mask is arranged in the slot corresponding to the left eye. In a left eye monocular test, an optical lens is arranged in the slot corresponding to the left eye whereas a mask is arranged in the slot corresponding to the right eye. In a binocular test, an optical lens is arranged in each of the two slots.

Method According to the First Aspect of the Invention

Figure 1:
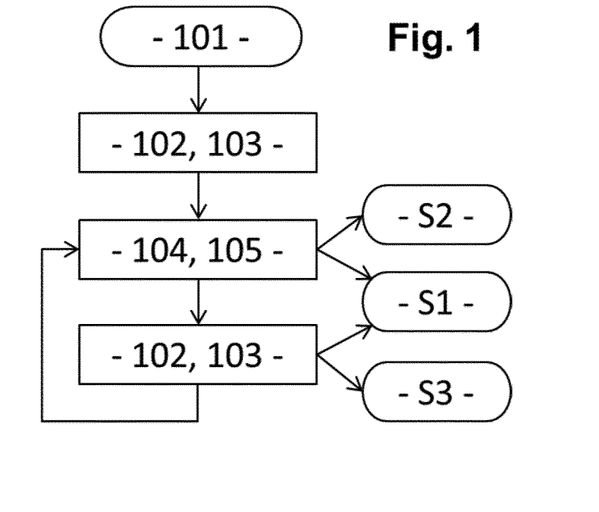
FIG. 1 shows a diagram of the steps of the method according to the first aspect of the invention.

The method 100 according to the first aspect of the invention is implemented by means of an automatic refractor head T controlled by the control module according to the second aspect of the invention. FIG. 1 shows a diagram of the steps of the method 100.

Figure 2:
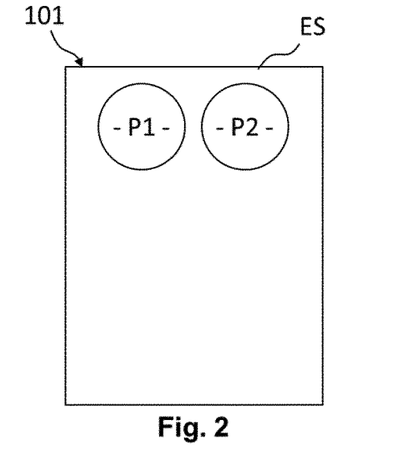
FIG. 2 shows an example of display by the control module of a first optical lens and a proposal for a second optical lens on a screen for selecting a proposal.

According to a first step 101 illustrated in FIG. 2, the control module displays on the selection screen ES a proposal P1 for a first optical lens V1 and a proposal P2 for a second optical lens V2.

Figure 3A:
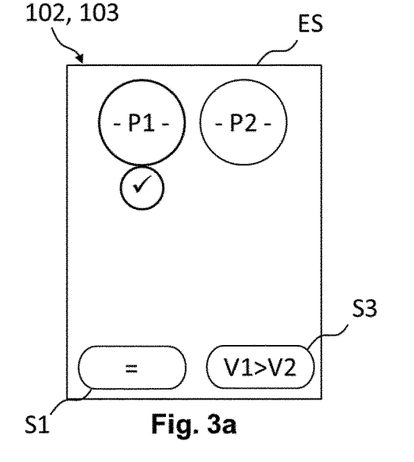
FIG. 3a shows an example of display by the control module of first and third validation symbols on the selection screen, when the proposal for the first optical lens is selected.
Figure 3B:
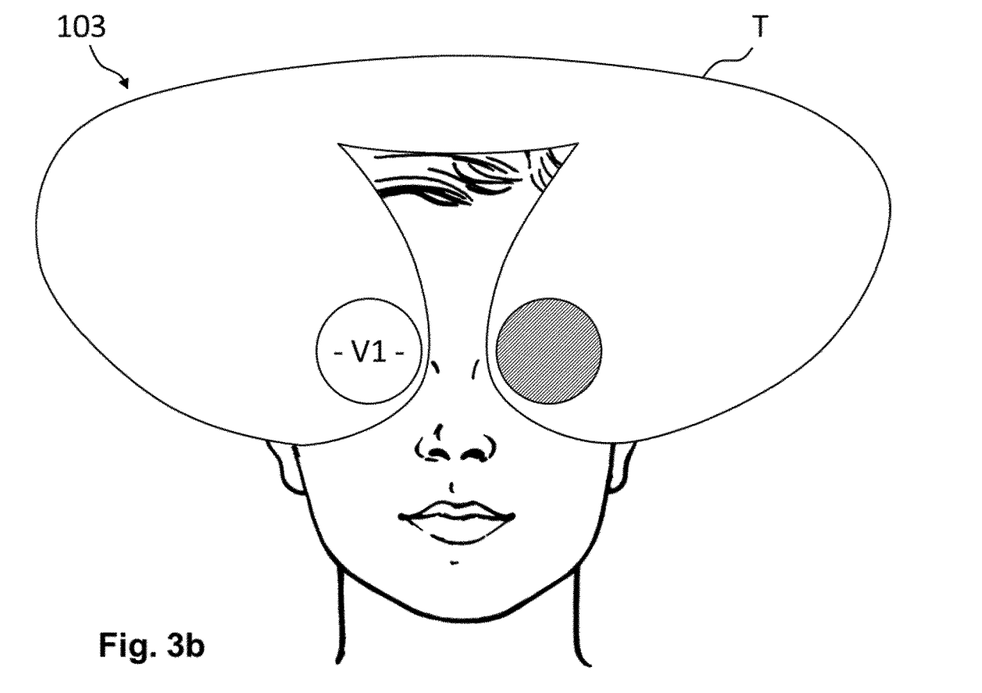
FIG. 3b shows an arrangement for a first optical lens in a slot of a support, according to a third step of the method according to the first aspect of the invention.

According to a second step 102 illustrated in FIG. 3a, the operator selects the proposal P1 for the first optical lens V1 and the control module receives the selection of the proposal P1 for the first optical lens V1. According to the second step 102 when it takes place of the first time, the proposal P1 for the first optical lens V1 is preferentially automatically selected, without intervention of the operator. According to a third step 103, on reception of the selection of the proposal P1 for the first optical lens V1, the control module arranges said first optical lens V1 in a slot of the automatic refractor head T. If this slot is already occupied by another element, the control module begins by removing the other element in order to be able to put in place the first optical lens V1. FIG. 3b illustrates the arrangement according to the third step 103.

According to the third step 103 when it takes place of the first time, on reception of the selection of the proposal P1 for the first optical lens V1, the control module further preferentially displays on the selection screen ES first and third validation symbols S1, S3, the first symbol S1 indicating that the first and second lenses V1, V2 are the same, the third symbol S3 indicating that the first optical lens V1 is better than the second optical lens V2, without however the displayed first and third validation symbols S1, S3 being selectable. FIG. 3a illustrates this preferential display. A second validation symbol S2 indicating that the second optical lens V2 is better than the first optical lens V1 could be displayed in addition while not being selectable either. Alternatively, according to the third step 103 when it takes place for the first time, on reception of the selection of the proposal P1 for the first optical lens V1, the control module displays no validation symbol on the selection screen ES.

Figure 4A:
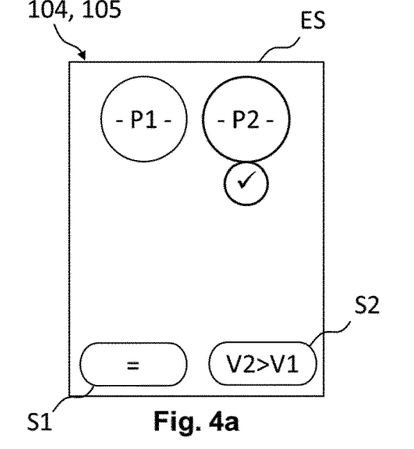
FIG. 4a shows an example of display by the control module of first and second validation symbols on the selection screen, when the proposal for the second optical lens is selected.

According to a fourth step 104 illustrated in FIG. 4a, the control module receives a selection of the proposal P2 for the second optical lens V2. According to a fifth step 105, on reception of the selection of the proposal P2 for the second optical lens V2, the control module arranges said second optical lens V2 in the slot of the automatic refractor head T beginning by removing the first optical lens V1. FIG. 4a illustrates the arrangement according to the fifth step 105.

According to the fifth step 105, on reception of the selection of the proposal P2 for the second optical lens V2, the control module further displays on the selection screen ES the first validation symbol S1 and a second validation symbol S2 indicating that the second optical lens V2 is better than the first optical lens V1, each of the first and second symbols S1, S2 being selectable. Conversely, the third validation symbol S3, which makes it possible to indicate that the first lens V1 is better than the second lens V2, is not selectable and in a preferential manner is not displayed at all. FIG. 4a illustrates this preferential display.

After the fifth step 105, the control module may:
- either receive a selection of the first validation symbol S1, which terminates the comparison method 100 while indicating that the first and second optical lenses V1, V2 are the same;
- or receive a selection of the second validation symbol S2, which terminates the comparison method 100 while indicating that the second optical lens V2 is better than the first optical lens V1;
- or receive again the selection of the proposal P1 for the first optical lens V1 according to the second step 102, and arrange the first optical lens V1 in the slot of the automatic refractor head according to the third step 103 beginning this time by removing the second optical lens V2.

According to the third step 103 when it takes place for the second time or more, on reception of the selection of the proposal P1 for the first optical lens V1, the control module further displays on the selection screen ES the first validation symbol S1 and a third validation symbol S3 indicating that the first optical lens V1 is better than the second optical lens V2, each of the first and third symbols S1, S3 being selectable. Conversely, the second validation symbol S2, which makes it possible to indicate that the second optical lens V2 is better than the first optical lens V1, is not selectable and in a preferential manner it is not displayed at all. FIG. 3a illustrates this preferential display.

After the third step 103, when it takes place for the second time or more, the control module may:
- either receive a selection of the first validation symbol S1 indicating that the first and second optical lenses V1, V2 are the same;
- or receive a selection of the third validation symbol S3 indicating that the first optical lens V1 is better than the second optical lens V2,
- or receive again the selection of the proposal P2 for the second optical lens V2 according to the fourth step 104, and arrange the second optical lens V2 in the slot of the automatic refractor head according to the fifth step 105 beginning by removing the first optical lens V1.

Figure 4B:
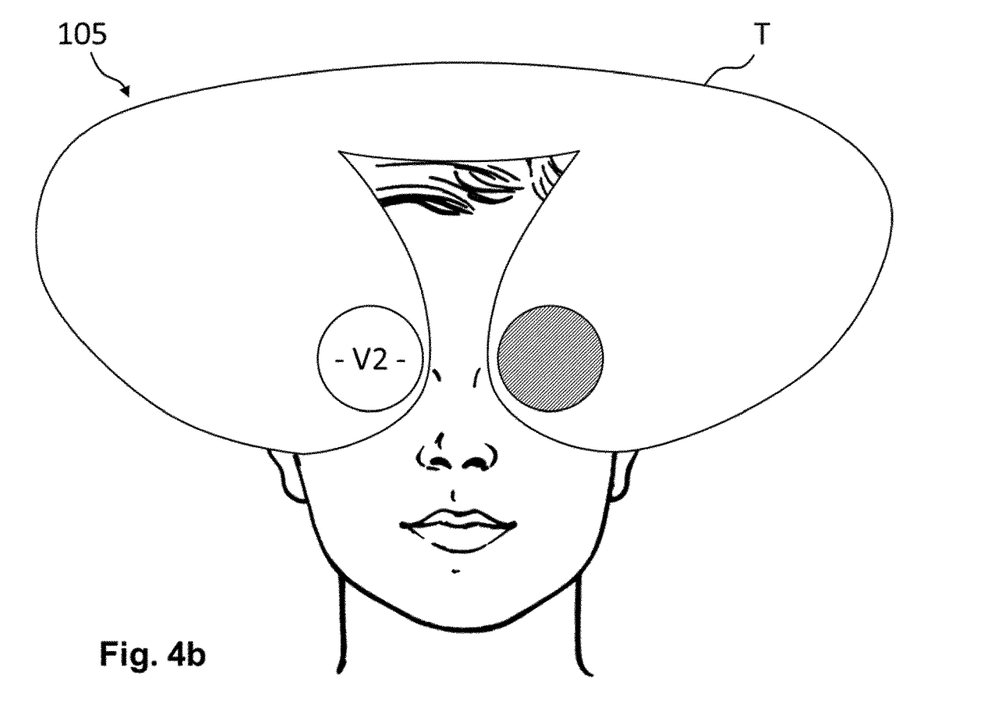
FIG. 4b shows an arrangement for a second optical lens in the slot of the support, according to a fifth step of the method according to the first aspect of the invention.

FIGS. 3*b* and 4*b* show an example according to which the automatic refractor head is used in a right eye monocular test: the first and second optical lenses V1, V2 are successively arranged in the slot corresponding to the right eye whereas the slot corresponding to the left eye is occupied by an opaque mask. The invention naturally also applies to the left eye monocular case, by arranging successively the first and second optical lenses V1, V2 in the slot corresponding to the left eye whereas the slot corresponding to the right eye is occupied by an opaque mask; and in the binocular test, by testing a first set of a first optical lens for the right eye and a first optical lens for the left eye, then a second set of a second optical lens for the right eye and a second optical lens for the left eye. In the case of a binocular test, the first optical lens for the right eye and the first optical lens for the left eye may be identical or different; similarly the second optical lens for the right eye and the second optical lens for the left eye may be identical or different.

Control Module According to the Second Aspect of the Invention

The control module according to the second aspect of the invention comprises for its part means for displaying simultaneously on the selection screen ES the proposal P1 for the first optical lens V1, the proposal P2 for the second optical lens V2 and all or part of the validation symbols S1, S2, S3 each indicating a possible result of a comparison between the first and second optical lenses V1, V2, preferentially either the first and second symbols S1, S2, or the first and third symbols S1, S3.

The control module according to the second aspect of the invention also comprises means for receiving a selection of the proposal P1, P2 for the first or the second optical lens V1, V2 or a validation symbol S1, S2, S3. The control module can only receive a selection of a proposal P1, P2 or a symbol S1, S2, S3 if said proposal or said symbol is displayed beforehand. Every proposal displayed is selectable but every symbol displayed is not necessarily selectable.

Finally, the control module according to the second aspect of the invention comprises means for, on reception of the selection of the proposal P1, P2 for the first or the second optical lens V1, V2, arranging said first or second optical lens V1, V2 in a slot of the automatic refractor head T.

In a preferential manner, the control module according to the second aspect of the invention comprises means for displaying a test symbol or a plurality of test symbols on the reading screen. The control module according to the second aspect of the invention may also comprise means for duplicating on the reading screen all or part of the display produced on the selection screen and/or for duplicating on the selection screen all or part of the display produced on the reading screen.

Furthermore, the display means on the selection screen ES and reception of a selection are such that:
  when the control module receives the selection of the proposal P1 for the first optical lens V1 for the first time, the proposal P2 for the second optical lens V2 is selectable on the selection screen ES and no validation symbol S1, S2, S3 is selectable on the selection screen ES;
  when the control module receives the selection of the proposal P2 for the second optical lens V2, the proposal P1 for the first optical lens V1 is selectable on the selection screen ES and the first and second validation symbols S1, S2 are selectable on the selection screen ES.
  when the control module receives the selection of the proposal P1 for the first optical lens V1 for the second time or more, the proposal P2 for the second lens V2 is selectable on the selection screen ES and the first and third symbols S1, S3 are selectable on the selection screen ES.

Selection Screen and Reading Screen

The operator interacts with the selection screen ES to select a displayed proposal P1, P2 or symbol S1, S2, S3. The examined subject interacts for his part with the reading screen to read or identify, through the automatic refractor head T, one or more displayed test symbols.

The selection screen ES and the reading screen are preferentially two distinct screens, for example a tablet for the selection screen ES and a projection screen for the reading screen. In this case, the display produced on the selection screen ES and on the reading screen may be identical or differentiated.

Alternatively, the selection screen ES and the reading screen may be a single and same screen, for example a projection screen, thus with a single and unique display.

Operator and Examined Subject

The operator is defined as being the person who interacts with the selection screen ES and with the control module. The operator is typically a practitioner, such as an ophthalmologist, an optician or even, within the scope of the present invention, an assistant without particular skills in the physics of refraction and the physiology of the visual system. The examined subject is defined as being the person who looks at the reading screen through the automatic refractor head T. The examined subject is typically a patient or client of the practitioner.

The examined subject may himself be the operator. The examined subject may be the only operator in the absence of any practitioner. Alternatively, two distinct operators, for example the examined subject and a practitioner, can relay with each other. When the examined subject is the operator, either the reading screen forms a single and same screen with the selection screen, or the reading screen is a second selection screen.

Markers on the Reading Screen

Preferentially, the control module comprises means for displaying on the reading screen:
  a first marker specific to the proposal P1 for the first optical lens V1 on reception of the selection of the proposal P1 for the first optical lens V1, and
  a second marker specific to the proposal P2 for the second optical lens V2 on reception of the selection of the proposal P2 for the second optical lens V2.

The first and second markers enable the examined subject to know which proposal for lens he is in the course of testing.

The first and second markers have a size which is adjusted in order that their angle of discrimination is sufficiently large to be perceived by the examined subject even if he does not manage furthermore to read or identify the test symbols. The first and second markers are preferentially displayed in distinct first and second zones of the reading screen.

System According to the Third Aspect of the Invention

The system according to the third aspect of the invention comprises the control module according to the second aspect of the invention as well as the selection screen ES.

The selection screen ES may be integrated with the control module. This is for example the case of a control module in the form of touch tablet or portable computer. Alternatively, the selection screen ES may be distinct from the control module. This is for example the case of a control module connected with a remote screen of computer screen, television screen or projection screen type.

The system according to the third aspect of the invention may also comprise the reading screen. In this case, the selection screen ES and the reading screen may be a single and same screen or two distinct screens.

Selection Steps and Means

Each step of selection, either of a proposal P1, P2 for a lens or a validation symbol S1, S2, S3, is carried out by the operator performing a selection action in interaction with the selection screen ES. The selection action may be carried out in different ways, of which several non-limiting examples are listed hereafter.

If the selection action is carried out on a selectable proposal P1, P2 or validation symbol S1, S2, S3, it leads to the transmission of a selection to the control module, which takes it into account by carrying out the steps of display and/or arrangement such as described previously. If the selection action is carried out on a proposal P1, P2 or a validation symbol S1, S2, S3 which is not selectable, it does not lead to any transmission of selection to the control module.

Moreover, if the selection action is carried out on a selectable proposal P1, P2 or validation symbol S1, S2, S3, it preferentially leads to a graphic modification of the appearance of the display in such a way as to inform the operator that his selection action has worked, whereas if the selection action is carried out on a non-selectable proposal P1, P2 or validation symbol S1, S2, S3, it does not lead to any graphic modification of the appearance of the display in such a way as to inform the operator that his selection action has not worked.

The selection action is preferentially carried out by means of a selection touch screen ES: the operator touches a zone of the screen on which is found a proposal P1, P2 for a lens or a validation symbol S1, S2, S3 in order to select said proposal or said validation symbol.

Alternatively, the selection action may be carried out by means of an interface which is for example:

- of mouse type: the operator positions the cursor of the mouse on the zone of the screen on which is found the proposal P1, P2 for a lens or the validation symbol S1, S2, S3 and clicks on this zone in order to select said proposal or said validation symbol; or
- of keyboard type: each proposal P1, P2 for a lens is identified by a key or combination of keys that is specific thereto, for example the key "1" for the proposal P1 for the first lens and the key "2" for the proposal P2 for the second lens; similarly, the first validation symbol S1 (that which indicates that the first and second optical lenses are the same) is identified by a key or combination of keys that is specific thereto, for example the "space" key. Since the second and third validation symbols S2, S3 are not simultaneously selected, they are for their part advantageously both identified by a single and same key or combination of keys that is specific thereto, for example the "entry" key. The operator presses on a key or combination of keys in order to select the corresponding proposal or validation symbol.
- of directional handle or joystick type: each proposal P1, P2 for a lens is identified by a direction that is specific thereto, for example towards the left for the proposal P1 for the first lens and towards the right for the proposal P2 for the second lens, the directions corresponding preferentially, if appropriate, to the first and second distinct zones of the reading screen on which are displayed the first and second markers. The directional handle also comprises a first button making it possible to select the first symbol S1 and a second button making it possible to select the second symbol S2 or the third symbol S3. The operator orients the directional handle in a given direction in order to select the corresponding proposal, or presses on a button in order to select the corresponding validation symbol.

According to another alternative, the selection is carried out by means of a voice control, via a microphone type equipment and a suitable module for processing the signal in the control module: each proposal P1, P2 for a lens is identified by a word or group of words that is specific thereto, for example the word "one" for the proposal P1 for the first lens and the word "two" for the proposal P2 for the second lens; similarly, the first validation symbol S1 (that which indicates that the first and second optical lenses are the same) is identified by a word or group of words that is specific thereto, for example the word "same" or "equal". Since the second and third validation symbols S2, S3 are not simultaneously selectable, they are for their part both advantageously identified by a single and same word or group of words that is specific thereto, for example the word "better" or "validate". The operator says a word or group of words in order to select the corresponding proposal or validation symbol.

According to yet another alternative, the selection is made by means of a gestural control, via a camera type equipment and a suitable module for processing the signal in the control module. According to a first alternative, each proposal P1, P2 for a lens is identified by a position or a movement of the hand that is specific thereto, for example a raised index finger for the proposal P1 for the first lens and a raised index finger and middle finger for the proposal P2 for the second lens; similarly, the first validation symbol S1 (that which indicates that the first and second optical lenses are the same) is identified by a position or a movement of the hand that is specific thereto, for example a clenched fist. Since the second and third validation symbols S2, S3 are not simultaneously selectable, they are for their part advantageously both identified by a single and same position or movement of the hand that is specific thereto, for example a raised thumb. According to a second alternative, the operator uses a finger, for example his index finger, as a pointer in order to designate the zone of the screen on which is found the proposal or the validation symbol that he wishes to select. In each of the two alternatives, the operator positions his hand or makes a movement in order to select the corresponding proposal or validation symbol.

The different selection actions of the method 100 according to the first aspect of the invention may all be carried out in a single and same manner, for example by means of a selection touch screen. Alternatively, a combination of several different techniques may be used to carry out the different selection actions of the method 100, for example the actions of selection of a proposal via a selection touch screen or via a gestural control, and the actions of selection of a validation symbol via a voice control, etc.

The invention claimed is:

1. A method for comparing first and second optical lenses by an automatic refractor head controlled by a control module, the first and second optical lenses being successively arranged in a slot of the automatic refractor head corresponding to a same eye of a user, the method being implemented by the control module and comprising:

displaying on a selection screen a proposal for a first optical lens and a proposal for a second optical lens;

receiving a selection of the proposal for the first optical lens;

arranging the first optical lens in the slot of the automatic refractor head on reception of the selection of the proposal for the first optical lens;

receiving a selection of the proposal for the second optical lens;

arranging the second optical lens in the slot of the automatic refractor head on reception of the selection of the proposal for the second optical lens;

displaying on the selection screen a plurality of validation symbols each indicating a possible result of the comparison;

the method being such that:

when the control module receives the selection of the proposal for the first optical lens for the first time, the proposal for the second optical lens is selectable on the selection screen and no validation symbol is selectable on the selection screen;

when the control module receives the selection of the proposal for the second optical lens, the proposal for the first optical lens is selectable on the selection screen and first and second validation symbols are selectable on the selection screen, the first symbol indicating that the first and second optical lenses provide equivalent vision correction to the eye of the user and the second symbol indicating that the second optical lens provides better vision correction to the eye of the user than the first optical lens;

when the control module receives the selection of the proposal for the first optical lens for the second time or more, the proposal for the second optical lens is selectable on the selection screen and the first symbol and a third symbol are selectable on the selection screen, the third symbol indicating that the first optical lens provides better vision correction to the eye of the user than the second optical lens.

2. The method according to claim 1, wherein when the reception of the selection of the proposal for the first optical lens takes place for the first time, it is carried out automatically by the control module without intervention of an operator.

3. The method according to claim 1, wherein when the control module receives the selection of the proposal for the first optical lens for the first time, the control module displays no validation symbol on the selection screen.

4. The method according to claim 1, wherein when the control module receives the selection of the proposal for the second optical lens, the control module displays the first and second validation symbols but not the third validation symbol.

5. The method according to claim 1, wherein when the control module receives the selection of the proposal for the first optical lens for the second time or more, the control module displays the first and third validation symbols but not the second validation symbol.

6. A module for controlling an automatic refractor head for the implementation of a method for comparing first and second optical lenses successively arranged in a slot of the automatic refractor head corresponding to a same eye of a user according to claim 1, the control module being configured to:

display simultaneously on a selection screen a proposal for a first optical lens, a proposal for a second optical lens and all or part of a plurality of validation symbols each indicating a possible result of a comparison between the first and second optical lenses;

receive a selection of the proposal for the first or the second optical lens or a validation symbol;

on reception of the selection of the proposal for the first or the second optical lens, arrange said first or second optical lens in a slot of the automatic refractor head;

the display on the selection screen and the reception of the selection being such that:

when the control module receives the selection of the proposal for the first optical lens for the first time, the proposal for the second optical lens is selectable on the selection screen and no validation symbol is selectable on the selection screen;

when the control module receives the selection of the proposal for the second optical lens, the proposal for the first optical lens is selectable on the selection screen and first and second validation symbols are selectable on the selection screen, the first symbol indicating that the first and second optical lenses are provide equivalent vision correction to the eye of the user and the second symbol indicating that the second optical lens provides better vision correction to the eye of the user than the first optical lens;

when the control module receives the selection of the proposal for the first optical lens for the second time or more, the proposal for the second lens is selectable on the selection screen and the first symbol and a third symbol are selectable on the selection screen, the third symbol indicating that the first optical lens provides better vision correction to the eye of the user than the second optical lens.

7. A system for the implementation of a method for comparing first and second optical lenses, comprising the module for controlling an automatic refractor head according to claim 6 as well as the selection screen.

8. The system according to claim 7, further comprising a reading screen.

9. The system according to claim 8, wherein the selection screen and the reading screen are two distinct screens.

10. The system according to claim 8, wherein the selection screen and the reading screen are a single and same screen.

* * * * *